United States Patent
Rosen (10) Patent No.: US 6,991,778 B2
(45) Date of Patent: Jan. 31, 2006

(54) USE OF DENDRIMERS POLYL-FUNCTIONALIZED WITH NITROXIDE GROUPS AS CONTRAST ENHANCING AGENTS IN MRI IMAGING OF JOINTS AND INJECTABLE COMPOSITIONS COMPRISING THEM

(75) Inventor: Gerald M. Rosen, Lutherville, MD (US)

(73) Assignee: Nitrosci, Owings Mills, MD (US)

( * ) Notice: Subject to any disclaimer, the term of this patent is extended or adjusted under 35 U.S.C. 154(b) by 257 days.

(21) Appl. No.: 10/148,962
(22) PCT Filed: Dec. 6, 2000
(86) PCT No.: PCT/US00/32985
§ 371 (c)(1),
(2), (4) Date: Nov. 4, 2002
(87) PCT Pub. No.: WO01/41640
PCT Pub. Date: Jun. 14, 2001

(65) Prior Publication Data
US 2003/0215390 A1 Nov. 20, 2003

Related U.S. Application Data
(60) Provisional application No. 60/169,976, filed on Dec. 10, 1999.

(51) Int. Cl.
*A61B 5/055* (2006.01)

(52) U.S. Cl. .................................. 424/9.3; 424/9.33
(58) Field of Classification Search ............... 424/9.33, 424/9.3, DIG. 16; 600/420
See application file for complete search history.

(56) References Cited

U.S. PATENT DOCUMENTS

| | | | |
|---|---|---|---|
| 5,104,641 A | | 4/1992 | Rosen |
| 5,256,397 A | * | 10/1993 | Rosen ..................... 424/9.33 |
| 5,527,524 A | | 6/1996 | Tomalia et al. |
| 5,567,411 A | | 10/1996 | Keana et al. |

OTHER PUBLICATIONS

A. W. Bosmann et al., "Five Generations of Nitroxyl-Functionalized Dendrimers", Macromolecules, American Chemical Society, Easton, US, vol. 30, No. 12, pp. 3606–3611, Jun. 16, 1997, XP000700749.

* cited by examiner

Primary Examiner—Michael G. Hartley
(74) Attorney, Agent, or Firm—Millen, White, Zelano & Branigan, P.C.

(57) ABSTRACT

The image obtained by MR imaging of the joint of an animal, including humans, is enhanced by injecting into the joint prior to the scan of an imaging enhancing amount of a nitroxyl functionalized dendrimer containing at least 6 nitroxyl terminal functional groups, e.g, of Formula (I) wherein each R independently is either a nitroxyl group of Formula (II) wherein X is an oxygen atom or two hydrogen atoms, R' is lower alkyl and R" is H or lower alkyl, or a group of Formula (III) wherein R'" is lower alkyl, or a group of Formula (IV); wherein each alkylene in Formulae (I), (III) and (IV) is a bridging divalent alkylene group of 2–6 carbon atoms with 2–3 carbon atoms in the chain and R is as defined herein, with the proviso that the total number of R groups in the molecule which are nitroxyl groups of Formula (II) is at least 6

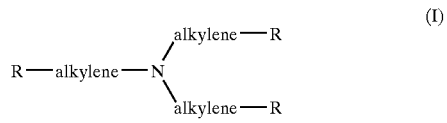

(I)

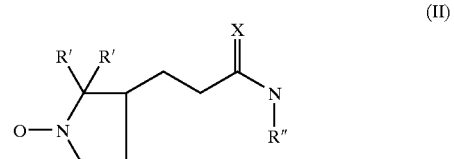

(II)

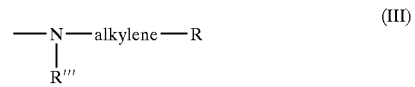

(III)

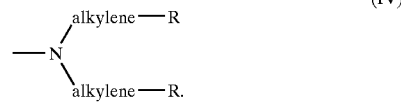

(IV)

15 Claims, 3 Drawing Sheets

USE OF DENDRIMERS POLYL-FUNCTIONALIZED WITH NITROXIDE GROUPS AS CONTRAST ENHANCING AGENTS IN MRI IMAGING OF JOINTS AND INJECTABLE COMPOSITIONS COMPRISING THEM

This application is the U.S. National Stage of International Application PCT/US00/32985 of Dec. 6, 2000 which claims benefit of U.S. Provisional Application Ser. No. 60/169,976 of Dec. 10, 1999.

This invention relates to the use of poly-nitroxyl-functionalized dendrimers as contrast enhancing agents for Magnetic Resonance Imaging (MRI) for the evaluation of degenerative joint diseases, such as osteoarthritis or rheumatoid arthritis.

Normal articular cartilage is a critical component of efficient, painless joint function. Pathologically, osteoarthritis is characterized by progressive loss of articular cartilage. Recent advances in understanding the pathogenesis of osteoarthritis have suggested that, in the near future, the development of drugs that will be able to reverse pre-existing abnormalities in articular cartilage or prevent their progression may be possible, if therapy is started early during the course of the disease. As a result, there is a tremendous need for a non-invasive technique that can accurately detect the presence of early cartilage abnormalities and the progression of those abnormalities in patients with osteoarthritis or rheumatoid arthritis. To date, radiography has been limited in its ability to accurately evaluate cartilage disorders, because cartilage can only be imaged indirectly. The osseous abnormalities (such as osteophyte formation) that eventually develop in patients with osteoarthritis are not sensitive indicators of early disease, nor are they reliable measures of disease progression.

Therefore, over the past several years, a great deal of attention has focused on the use of advanced cross-sectional imaging techniques, such as MRI for the assessment of abnormalities in articular cartilage. Numerous MRI sequences and techniques have been evaluated. Unfortunately, these studies have yielded variable, contradictory and often disappointing results. As a consequence, there is no universally accepted "best sequence or technique" for accurate MR imaging of articular cartilage. There are two contrast enhancing agents that one would logically consider in looking for a way to adapt MRI as a tool for evaluating the progression of osteoarthritis in a joint of a patient exhibiting the symptoms of the disease.

The first candidate one would logically consider, in view of its high relaxivity (ca. 5, room temperature, 1.5 T) is the commercially available MRI contrast agent gadolinium (Gd)-DTPA. However, inclusion of an intraarticular injection of gadolinium (Gd)-DTPA in the protocol of an MRI evaluation of the progression of osteoarthritis in a joint of a patient exhibiting the symptoms of the disease only modestly improves the evaluation of proteoglycan status and cartilage morphology. This is due to the inability of Gd-DTPA to effectively bind to proteoglycans in the joint. Because proteoglycan molecules within the cartilage matrix are negatively charged and are responsible for the fixed charge density (FCD) of the cartilage matrix that is associated with proteoglycan loss and Gd-DTPA is also negatively charged. Since two negatively charged molecules repel each other, if one wishes to use Gd-DTPA as the contrast agent, alternative methods must be developed. Bashir, et al., *Magn. Reson. Med.* 36: 665–673, 1996, have shown that Gd-DTPA distributes in cartilage inversely proportional to the local FCD. Since the negatively charged proteoglycans will repel the Gd-DTPA, areas of proteoglycan depletion will demonstrate relative enhancement when compared to more normal regions. Bashir, et al., *Radiology* 205: 551–558, 1997. However, this technique is limited in that the diffusion of the contrast into the cartilage is quite slow. Even though more rapid enhancement of the cartilage is possible with intravenous injection of the contrast media, equilibration throughout the cartilage still requires about 5 hr. Additionally, with this technique, the abnormal cartilage appears bright while the normal cartilage appears dark, potentially leading to confusion between incomplete diffusion of the contrast into normal cartilage and abnormal superficial portion of the cartilage. Thus, Gd-DTPA, although very potent as a MRI contrast enhancing agent generally, is very poor as a tool for evaluating degenerative joint diseases, such as osteoarthritis, due to its lack of specificity for proteoglycans, which results in a high concentration of the Gd-DTPA in equilibrium within the joint space and the surface of the joint where the proteoglycans are located, which has prompted the commercially unattractive manipulations as noted above.

Another class of MRI contrast enhancing agents which one might consider for injection into a joint are the nitroxides. However, nitroxides as a class are not a likely candidate because they are rapidly reduced enzymatically in tissues into products which do not enhance an MR image (Griffeth, et al., *Invest. Radiol.* 19: 553–562, 1984) and, like Gd-DTPA, have no specificity with respect to cartilage proteoglycans in joints. Therefore, as a class nitroxides are not suitable for use in evaluating the progress of a joint degenerative disease by MRI of a joint of a patient with such a disease.

An exception to this general rule with respect to the lack of resistance of nitroxides to enzymatic reduction are the positively-charged nitroxides which are the subject of my prior U.S. Pat. Nos. 5,104,641 and 5,256,397. Moreover, because these MRI contrast enhancing agents are positively-charged, in contrast to a gadolinium-based contrast agent and nitroxides generally, they can bind to the negatively-charged proteoglycan and thus have the potential of being a useful tool in joint degenerative disease evaluation.

U.S. Pat. Nos. 5,104,641 and 5,256,397 detail the use of positively charged nitroxides as MRI contrast enhancing agents for the evaluation of degenerative joint disease. In U.S. Pat. No. 5,256,397 and Pou, et al., (*Free Rad. Res.* 23: 353–364, 1995), the inventor described the remarkable in vivo stability of one member of a family of positively charged nitroxides, 3-trimethylaminomethyl-2,2,5,5-tetramethyl-1-pyrrolidinyloxyl iodide (whose synthesis is described in U.S. Pat. No. 5,256,397) and its long-lifetime in a knee joint of a rabbit. More recently, the inventor in Bacic, et al. (*Magn. Reson. Med.* 37: 764–768, 1997) demonstrated the high affinity of 3-trimethylaminomethyl-2,2,5,5-tetramethyl-1-pyrrolidinyloxyl iodide toward proteoglycans in rabbit joints. Here, unlike the negatively-charged Gd-DTPA, the positively charged nitroxide, 3-trimethylaminomethyl-2,2,5,5-tetramethyl-1-pyrrolidinyloxyl iodide, was able to specifically bind to proteoglycans and as the result of proteoglycan degeneration caused by papain (a protease that breaks down proteoglycan thereby mimicking osteoarthritis), this positively charged nitroxide was able to follow the progression of proteoglycan loss in the rabbit joint.

However, the potency of these positively charged nitroxides as an MRI contrast enhancing agent is very low compared to a gadolinium-based contrast agent because of their low relaxivity ($^-0.2$ mM$^{-1}$ sec$^{-1}$ for nitroxides vs. 4.95 mM$^{-1}$ sec$^{-1}$ for Gd-DTPA), as reported by Keana, et al., (*Magn. Reson. Med.* 5: 525–536, 1987) which is a measure of contrast enhancing activity. Thus, as later reported by Pou, et al., (*Free Rad. Res.* 23: 353–364, 1995) and Bacic, et al. (*Magn. Reson. Med.* 37: 764–768, 1997) a very high dose (1 mL of a 10 mM stock solution of 3-trimethylaminomethyl-2,2,5,5-tetramethyl-1-pyrrolidinyloxy iodide) is essential to achieve an acceptable level of MRI contrast enhancing activity. Such high doses are not feasible clinically. Moreover, even if this fact alone did not preclude their use in joints to evaluate the progress of a joint degenerative disease, the high dose required to achieve a satisfactory level of image contrast enhancement would result in such a high concentration of the nitroxide in equilibrium between the joint space and the surface of the joint where the proteoglycans are located that the requisite selectivity of binding to the proteoglycans, which is necessary to permit evaluation of the progress of the degenerative disease in a joint cannot be achieved with these charged nitroxides, would not be present. Therefore, even the charged nitroxides, which are useful as MRI contrast enhancing agents generally, including in joints, are of little practical value in assisting in the evaluation of the degenerative progress in the joint of a patient afflicted with a joint degenerative disease, because this end use requires a dose which is low enough to achieve selective binding to the proteoglycans while still enhancing to a clinically acceptable level the MR image achieved.

There are other nitroxides known in the prior art besides those of my prior issued patents cited above. One class are the calixarene conjugates containing a plurality of imaging substituents, e.g., gadolinium or nitroxyl groups, which are disclosed as MRI and CT diagnostic imaging agents in U.S. Pat. Nos. 5,622,687 and 5,846,515. Another class are the poly-nitroxyl-functionalized dendrimers described by Bosman, A. W., et al., *Macromolecules* 1997, 30, 3606–3611, whose MRI contrast enhancing activity has not been reported in the literature. Both disclose compounds which possess as their nitroxyl-functionalizing group the same 1-oxyl-2,2,5,5-tetramethyl4-substituted-pyrrolidine group as some of the mono-nitroxides of my two patents cited above. However, because of the loss of selectivity which occurs at the high concentration in the joint required to achieve a clinically acceptable level of MRI contrast enhancement in the case of the corresponding mono-nitroxides (due to their low relaxivity), one would expect that the increased concentration of such nitroxyl groups in a joint provided by the presence of a plurality of these nitroxyl groups in a calixarene or dendrimer molecule as functionalizing groups would have the same adverse effect on the selectivity of the MRI imaging achieved in a degenerative joint as reported for the mono-nitroxides of my prior patents.

Consequently, neither a nitroxide nor a gadolinium-based MRI contrast enhancing agent has been reported in the literature to be of practical value as a tool for the specific purpose of evaluating the progress of osteoarthritis in the joint of a patient, which requires the unique combination of resistance to enzymatic reduction, a high relaxivity value and selectivity with respect to binding to the proteoglycans present in a joint. However, I have found that, surprisingly, increasing the number of nitroxyl-functionalizing groups on a dendrimer not only increases the relaxivity of the dendrimer, it does so while retaining its resistance to enzymatic reduction and without decreasing its selectivity to the proteoglycan in the joint of a patient exhibiting the subjective symptoms of a joint degenerative disease, such as osteoarthritis or rheumatoid arthritis.

OBJECT OF THE INVENTION

Accordingly, it is an object of this invention to provide an improvement in a method of enhancing the image obtained by MRI of the joint of an animal, including humans, which employs a nitroxide compound as imaging enhancing agent. Another object is the provision of a method of accurately MR imaging the articular cartilage of a joint of a patient exhibiting symptoms of osteoarthritis, rheumatoid arthritis or like bony degradation disease. Other objects will be apparent to those skilled in the art to which this invention pertains.

SUMMARY OF THE INVENTION

In a method aspect, this invention relates to a method of enhancing the image obtained by MRI of the joint of an animal, exhibiting symptoms of a disease which causes degeneration of the joints, which method comprises injecting, in admixture with a non-toxic injectable pharmacologically acceptable vehicle, into the joint of the animal, including humans, prior to the MRI scan of the joint, an image enhancing amount which is effective both to enhance the MRI produced by the scan and to visualize the proteoglycan in the joint, of a water soluble or water dispersible nitroxyl-functionalized dendrimer having at least 6 PROXYL-nitroxyl groups as terminal groups, e.g., of the Formula (I):

(I)

wherein each R independently is (A) a nitroxyl group of the formula:

(II)

in which R' is lower alkyl and R" is H or lower alkyl and X is an oxygen atom or two hydrogen atoms, or (B) a group of Formula (III):

(III)

wherein R''' is lower alkyl, or (C) a group of Formula (IV)

(IV)

wherein each alkylene in Formulae (I), (III) and (IV) is a bridging divalent alkylene group of 2–6 carbon atoms with 2–3 carbon atoms in the chain and R is as defined hereinabove, with the proviso that the total number of R groups in the molecule which are nitroxyl groups of Formula (II) is at least 6.

In another method aspect, this invention relates to an improvement in a method of enhancing the image obtained by MRI of a joint of a human exhibiting symptoms of osteoarthritis or rheumatoid arthritis by injecting into the joint, prior to the MRI scan thereof, in admixture with a non-toxic injectable pharmacologically acceptable vehicle, an image enhancing amount which is both non-toxic and effective to enhance the MR image produced by the scan, of a water soluble organic nitroxide, which improvement comprises employing as the nitroxide, a poly-nitroxyl-functionalized dendrimer of Formula (I).

DETAILED DESCRIPTION

Figure 1:
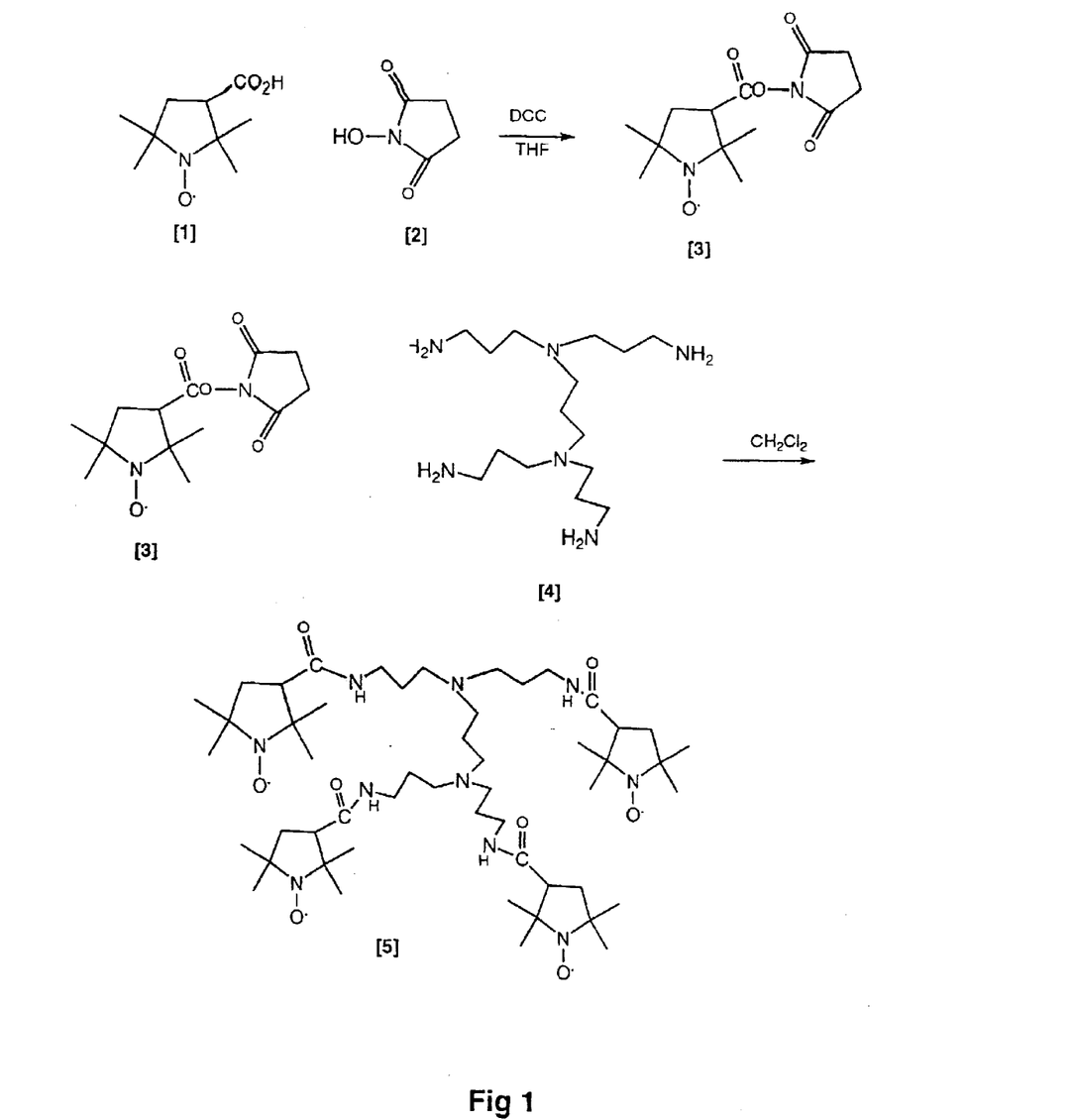
FIG. 1 is a flow sheet of a method for producing the PROXYL-functionalized dendrimer containing 4 nitroxide groups wherein X=O employed in the method of this invention.
Figure 2:
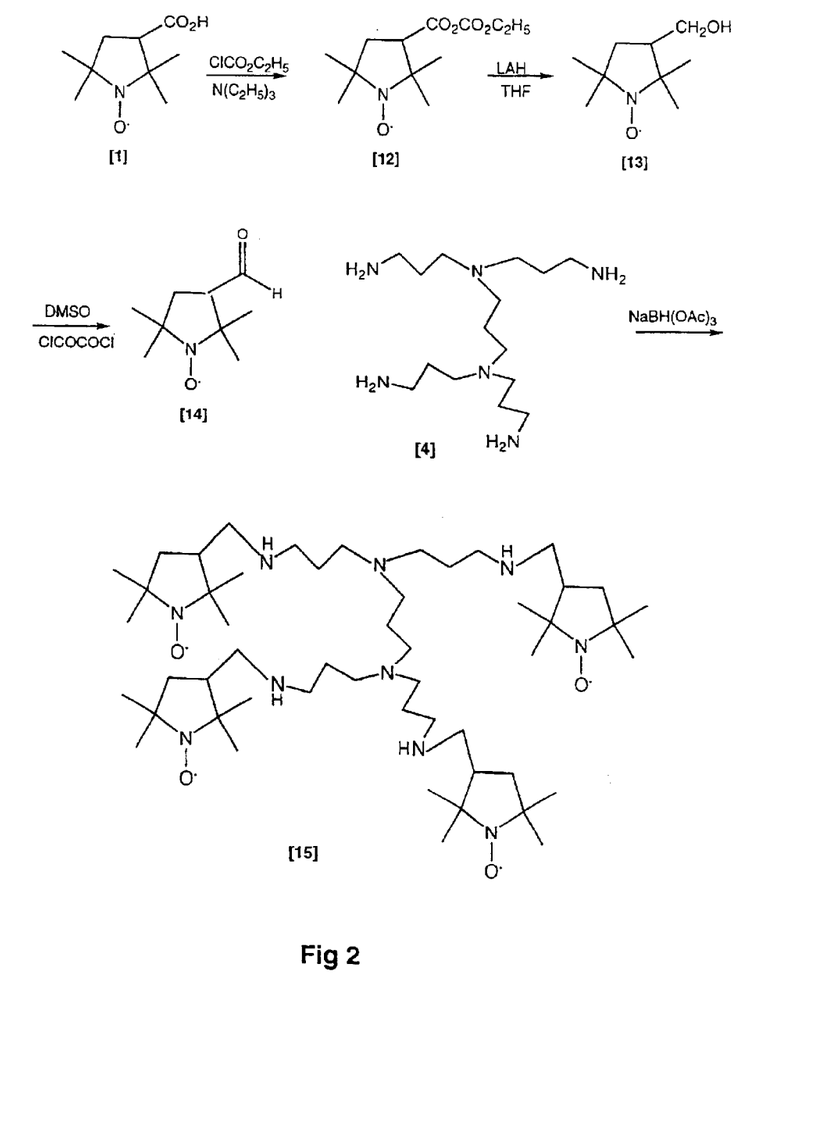
FIG. 2 is a flow sheet of a method for producing the PROXYL-functionalized dendrimer containing 4 nitroxide groups wherein X=H, H employed in the method of this invention.
Figure 3:
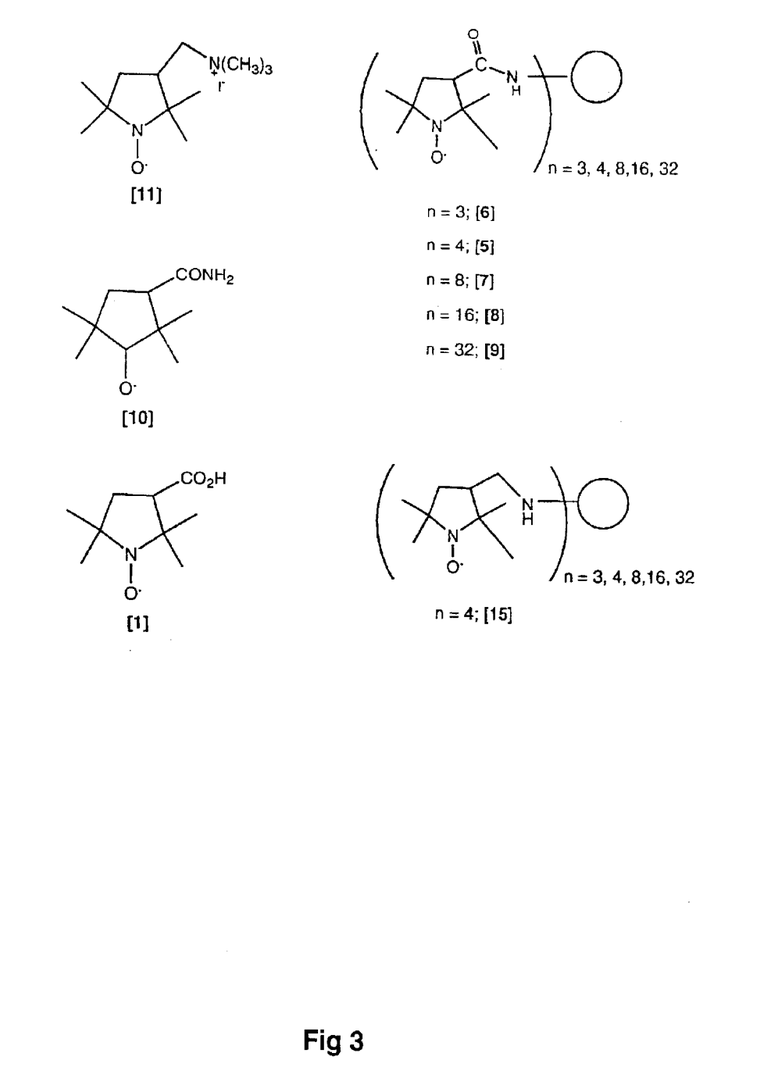
FIG. 3 shows the generic formulae for the dendrimers of FIGS. 1 and 2 wherein n indicates the number of nitroxide groups in the molecule and three 3-substituted-PROXYL monomers.

As noted above, some of the nitroxyl-functionalized dendrimers employed in the method of this invention are members of a known class of poly(propyleneimine) (DAB) terminal functionalized with 3-CO-"PROXYL" nitroxyl groups, i.e. 2,2,5,5-tetramentyl-1-pyrrolidinyloxy, groups of the formula DAB-dendr-(NH-3-CO-PROXYL)$_n$ (V) wherein "n" is a positive integer, some of whom and their preparation are described by A. W. Bosman, et al. (1997), supra, whose disclosure is incorporated herein by reference. The prior art dendrimers all are symmetrical, which means that is "n" is an even number. However, corresponding unsymmetrical species can be prepared, e.g., by using an equivalent excess (based on the terminal amino groups of the non-functionalized dendrimer reactant) precursor relative to the 3-CO-PROXYL functionalizing reactant, which will result in the production of a functionalized dendrimer in which one or more of the terminal groups are amino groups and the remainder are —NH-3-CO-PROXYL groups. Other conventional methods can be used to produce multiple generation symmetrical and unsymmetrical fully and partially functionalized dendrimers.

Because they possess unfunctionalized amino groups, the nitroxyl-functionalized dendrimers employed in the method of this invention are "positively charged", i.e., in addition to the nitroxyl group, they possess a plurality of amino groups which, at physiological pH, are positively charged. Preferably, they have a pKa value greater than 7.4. They also are stable, which means that they have an acceptable half-life when stored under ambient anhydrous conditions, e.g., greater than 2 years and preferably greater than 5 years, and are stable in aqueous solution for at least 1 hour, preferably 2 hours, and most preferably at least 8 hours.

These dendrimers are water soluble, preferably at least 100 μM, or water dispersible, e.g., as a colloidal suspension, e.g. in the case of the relatively high molecular weight of the dendrimers having a large number of nitroxyl groups, e.g., 48 or more. If it is desirable to increase the water solubility of those higher molecular weight dendrimers, as would be obvious to one skilled in the art solubilizing groups, e.g., quaternary ammonium groups, can be introduced into the molecule until the desired solubility is achieved.

The dendrimers employed in this invention are neurologically and physiologically non-toxic and preferably are substantially physiologically inert at the dose administered. They are bioreductive resistant, i.e., their half-life is preferably at least 2 hours and more preferably at least 4 hours in situ.

The term "lower alkyl" means from 1–8, preferably 1–6 and most preferably 1–4 carbons, with methyl, ethyl and isopropyl being preferred and methyl most preferred. The term "alkylene" as used herein refers to a divalent bridging hydrocarbon group having a total of from 2 to 6 carbon atoms of which 2 or 3 thereof are in the chain. Examples are ethylene, trimethylene, 1,2-isopropylene, 2,3-isopropylene, 1,2- and 2,3-butylene and 2,3-amylene.

The dendrimers of Formula (I) have exceptionally good relaxivities and resistance to reduction, as can be seen from data in Table I for the dendrimers listed therein.

TABLE 1

Relaxivities ($k_1$, room temperature, 1.5 T) and Rate of Nitroxide Reduction (micromolar/min, room temperature)

| Nitroxide | No. of Nitroxide Groups (n) | Relaxivity ($k_1$) | Reduction Rate (micromolar/min) |
|---|---|---|---|
| [5] | 4 | 0.82 | 7.93 |
| [6] | 3 | 0.57 | 7.54 |
| [7] | 8 | 1.69 | 0.00 |
| [8] | 16 | 3.19 | 0.00 |
| [9] | 32 | 5.73 | 0.00 |
| [10] | 1 | 0.19 | 8.00 |
| [11] | 1 | 0.19 | 0.00 |
| [15] | 4 | 0.82 | — |
| [1] | 1 | 0.19 | 0.52 |
| Gd(DTPA) | 0 | 4.94 | — |

In dendrimer compounds 5–9, in Formula (II) R'=methyl, R"=H and X=O, except in compound 15 in which X=H,H, and in Formula (I) alkylene tri-methylene and the three Rs are:

[5] (Formula II)$_2$, (Formula IV, each R is Formula II)

[6] (Formula II)$_3$

[7] (Formula IV in which each R is Formula II)$_2$, (Formula IV in which each R is Formula IV in which each R is Formula II)

[8] (Formula IV in which each R is Formula IV in which each R is Formula II)$_2$, (Formula IV, in which each R is Formula IV, in which each R is Formula IV, in which each R is Formula II)

[9]] (Formula IV in which each R is Formula IV in which each R is Formula IV in which each R is Formula II)$_2$, (Formula IV, in which each R is Formula IV, in which each R is Formula IV, in which each R is Formula IV, in which each R is Formula II)

[15] (See [5], above. where X=two hydrogens.

Examples of dendrimers of Formula (I) useful in the method of this invention are those wherein:

a) alkylene is trimethylene, 1-methylethylene, 2-methylethylene or 2,3-butylene, preferably trimethylene;

b) X is a divalent oxygen atom, including the compounds of Group a);

c) X is two hydrogen atoms, including the compounds of Group a);

d) R' is methyl, ethyl or isopropyl, including the compounds of Groups a), b) and c);

e) R" is H or methyl, including the compounds of Groups a), b), c) and d);

f) two and preferably all three of the R groups of Formula (I) are groups of Formula IV, including the compounds of Groups a), b), c), d) and e);

g) the terminal R groups all are nitroxyl groups of Formula (II), including the compounds of Groups a), b), c), d), e) and f);

h) the total number of R groups in the molecule is at least 16, of which at least 8 of the terminal R groups include at least 8 nitroxyl groups of Formula (II), e.g., 8–64, preferably 12–48, and most preferably 16–32, e.g. 6, 7, 8, 9, 10, 12, 14, 16, 18, 20, 22, 24, 26, 28, 30, 36, 48 and other odd and even integers up to 64 or higher, and most preferably those with symmetrical structures, which contain 6, 12, 36 or 48 nitroxyl groups, as well as 4, 8, 16, 32 or 64 nitroxyl groups (because of their ease of synthesis), including those of Groups a), b), c), d), e), f) and g); and i) in Formula (I) each alkylene is trimethylene and each R group is a group of Formula (IV) in which each alkylene is trimethylene and each R group is a group of Formula (II) or (IV) as defined above, including those of Groups a), b), c), d), e), f), g) and h).

Preferred embodiments of the method of this the invention also comprise one or more of the following:

a) the animal is a human being, including methods employing a dendrimer as defined in any of Groups a)–i), above;

b) the animal, who is preferably a human being, exhibits one or more symptoms of c) osteoarthritis or rheumatoid arthritis, including methods employing a dendrimer as defined in any of Groups a)–i) above; and c) the joint of the animal, who preferably is a human being, especially one exhibiting d) osteoarthritis or rheumatoid arthritis, is a knee or shoulder joint, including methods employing a dendrimer as defined in any of Groups a)–i), above.

The term "joint" as used herein embraces any joint as the medical term embraces, including joints of the fingers and toes, feet and hands, wrists and ankles, knees and elbows, neck, shoulders, back, and hips. Because the joints most frequently examined to evaluate their morphology are the knee and shoulder, these joints are a preferred aspect of the method of this invention.

The term "animal" preferably means a human being. However, other animals, ordinarily mammals, and particularly valuable domestic mammals, such as dogs, cats, race horses are also embraced by the term.

The dendrimer is ordinarily injected as a solution in a non-toxic injectable pharmacologically acceptable sterile aqueous vehicle, e.g., distilled water physiological saline solution or fluid withdrawn from the joint to be MRI scanned, or a mixture of either of the latter two or the former two. The aqueous vehicle can also contain other ingredients conventionally present in solutions which are injected into the joint, e.g., local anesthetic, anti-inflammatory agent, e.g., cortisone, antibiotic, stabilizing agent, suspending agent, etc.

The concentration of the dendrimer in the solution is usually from about 10 to 500 micromolar, preferably from about 20 to 250 micromolar, and more preferably from about 50 to 150 micromolar, e.g., about 100 micromolar The amount of dendrimer injected into the joint is influenced by the volume of the joint void, the concentration of the dendrimer in the solution injected into the joint and the reflectivity of the dendrimer. Generally speaking, at a concentration of 100 micromolar, a dose from a low of about 0.17 mg/mL for a dendrimer containing 16 nitroxyl groups injected into one of the joints of the hand to a high of about 0.89 mg/mL for a dendrimer containing 32 nitroxyl groups injected into the shoulder joint is employed. Knowing the in vitro image enhancing activity of the selected dendrimer and the dose required to obtain satisfactory MRI contrast enhancement in the joint with, for example, Gd-DTPA, a person knowledgeable MRI can readily predict the optimum dose for obtaining the desired degree of MRI contrast enhancement in a scan of that joint.

The nitroxyl-functionalized dendrimers employed in the method of this invention can be prepared in conventional ways known in the art, e.g., as described by Bosman, et al., *Macromolecules* 1997, 3606–3611, and as illustrated in the Examples hereinafter.

Conventional MRI scanning techniques now employed extensively to obtain MR images of joints can be employed. See, e.g., DiChino, G., et al., *Radiology* 1985 157:373–377; Portugal, F. H., *High Technology* August, 1984, pp. 66–73: and Katzberg, R. W., "*The Contrast Media Manual*" (Williams and Wilkins, Baltimore, Md., 1992). A non-toxic amount effective to enhance the MR image obtained but less than that at which selectivity, with respect to attraction to the proteoglycan molecules within the cartilage matrix is diminished.

A contemplated equivalent of the method of this invention is the use of the dendrimers used therein, particularly those containing a higher number of nitroxyl substituents, e.g., 16, 32, 48, 64 or even higher, as MRI contrast enhancing agents in which the contrast enhancing agent is delivered to the scanned organ or other tissue area by injection in the blood stream rather than in situ in a joint, e.g., as described in U.S. Pat. Nos. 5,104,641 and 5,256,397. The combination of the very high relaxivity achieved by the large number of nitroxyl substituents attached to dendrimers and the surprisingly high resistance to bioreduction in the blood of dendrimers having such a high number of nitroxyl substituents renders these dendrimers feasible for this purpose. Another contemplated equivalent is the use therein of a dendrimer otherwise corresponding to those of Formula (I) in which (a) the bridging groups in one or more of the generations of the dendrimer differ from the others; (b) one or more of the nitroxyl groups are positioned within the dendrimer core structure rather than as terminal groups; and/or (c) the dendrimer contains one or more non-interfering functional groups in addition to those present on the dendrimers used in the method of this invention, e.g., hydroxy, amino, alkoxy, halogen, nitro, etc., which does not adversely affect the solubility, relaxivity and selectivity of the nitroxyl-functionalized dendrimer.

Without further elaboration, it is believed that one skilled in the art can, using the preceding description, utilize the present invention to its fullest extent. The following preferred specific embodiments are therefore to be construed as merely illustrative and not limitative of the remainder of the disclosure in any way whatsoever. In the foregoing and in the following examples all temperatures are set forth uncorrected in degrees Celsius and, unless otherwise indicated, all parts and percentages are by weight. The entire disclosure of all applications, patents and publications cited herein are incorporated herein by reference.

EXAMPLES

Example 1

Synthesis of Dendrimer-Containing Nitroxides

3-[(2,5-Dioxo-1-pyrrolidinyl)oxy]carbonyl]-2,2,5,5-tetramethyl-1-pyrrolidinyloxyl [3]. To a solution of 3-carboxy-2,2,5,5-tetramethyl-1-pyrrolidinyloxyl [1], prepared as described in the literature, E. G. Rozantsev. *Free Nitroxyl Radicals*, Plenum Press, N.Y., pp. 203–206, (500 mg, 2.69 mmoles) dissolved in THF (50 mL) was added N-hydroxysuccinimide [2] (Aldrich Chemical Company, Milwaukee, Wis., 310 mg, 2.69 mmoles). After dissolution, 1,3-dicyclohexylcarbodiimide (Aldrich Chemical Company, 610 mg, 2.96 mmoles) was added. The reaction mixture was stirred for 2 days at room temperature, filtered and evaporated, in vacuo. The remaining oil was taken up in methylene chloride, filtered and evaporated in vacuo to dryness. The residue material was then washed with hot cyclohexane (3 times, 10 mL). The residual oil, dissolved in chloroform:hexane (80:20), was passed through a chromatographic column containing silica gel (Aldrich Chemical Company, mesh 230–400), removing remaining 1,3-dicyclohexylcarbodiimide. Elution with chloroform:acetone (96:4), afforded, after evaporation of the solvent, 3-[[(2,5-dioxo-1-pyrrolidinyl)oxy]carbonyl]-2,2,5,5-tetramethyl-1-pyrrolidinyloxyl [3] as a yellow oil, which solidified upon standing at room temperature (ref. 2). FT-IR: ($CHCl_3$) 1813, 1787 and 1744 (C=O) $cm^{-1}$; EPR: $A_N$=14.5 G.

DAB-dendrimer-(NH-3-CO-PROXYL)$_4$[5]. A solution of 3-[[(2,5-dioxo-1-pyrrolidinyl)oxy]-carbonyl]-2,2,5,5-tetramethyl-1-pyrrolidinyloxyl [3] (1.9 gm, 6.7 mmoles) and DAB-dendrimer-4 [4] (Aldrich Chemical Company, 480 mg, 1.52 mmoles) dissolved in methylene chloride (50 mL) was stirred at room temperature for 5 days. At this point, a saturated NaCl solution (10 mL) was added to the reaction and the layers separated, the organic phase was dried over anhydrous $Na_2SO_4$. Filtration followed by rotary evaporation to dryness gave an oil. Purification by column chromatography using silica gel (Aldrich Chemical Company, mesh 230-400) and chloroform:acetone (96:4), separated excess 3-[[(2,5-dioxo-1-pyrrolidinyl)oxy]carbonyl]-2,2,5,5-tetramethyl-1-pyrrolidinyl-oxyl [3] added to the reaction mixture. Changing to chloroform:methanol (50:50) afforded DAB-dendrimer-(NH-3-CO-PROXYL)$_4$ [5] as an oil, which solidified upon placement under high vacuum. EPR spectrum was broad with some definition of a 3-lined signal. A. W. Bosman, R. A. J. Janssen and E. W. Meijer. Five generations of nitroxyl-functionalized dendrimers. *Macromolecules*, 30: 3606–3611, 1997.

DAB-dendrimer-(NH-3-$CH_2$-PROXYL)$_4$[15]. To a solution of 3-carboxyaldehyde-2,2,5,5-tetramethyl-1-pyrrolidinyloxyl [14], prepared as described in the literature, Pou. et al., *Free Rad. Res.* 23: 353–364, 1995 (500 mg, 2.94 mmoles) dissolved in THF (70 mL) was added DAB-dendrimer-4 [4] (Aldrich Chemical Company, 183 mg, 0.58 mmoles) dissolved in methylene chloride (20 mL) and sodium triacetoxyborohydride (492 mg, 2.3 mmoles). After the addition was completed, 3A° molecular sieves were added and the reaction was stirred at room temperature for 5 days. At this point, the mixture was filtered, evaporated to dryness in vacuo. A saturated NaCl solution (10 mL) was added and the mixture was extracted with chloroform, dried over anhydrous $Na_2SO_4$. Filtration followed by rotary evaporation to dryness gave an oil. Purification by column chromatography using silica gel (Aldrich Chemical Company, mesh 230–400) and chloroform:acetone (96:4), separated excess 3-carboxyaldehyde-2,2,5,5-tetramethyl-1-pyrrolidinyloxyl [14] added to the reaction mixture. Changing to chloroform:methanol (50:50) afforded DAB-dendrimer-(NH-3-$CH_2$-PROXYL)$_4$ [15] as an oil, which solidified upon placement under high vacuum. EPR spectrum was broad with some definition of a 3-lined signal.

General Procedure for the Preparation of DAB-dendrimer-(NH-3-CO-PROXYL)$_n$.

Following the general method described above, other PROXYL-functionalized dendrimers were prepared and purified by flash chromatography using silica gel (Aldrich Chemical Company, mesh 230–400) and different solvent systems: (a) TREN-dendrimer-(NH-3-CO-PROXYL)$_3$ [6] tris(2-aminoethyl)amine, (Pressure Chemical Company, Pittsburgh, Pa.) chloroform:methanol (95:5); (b) DAB-dendrimer-(NH-3-CO-PROXYL)$_8$ [7] methanol: ammonium hydroxide (30%) (98:2); (c) DAB-dendrimer-(NH-3-CO-PROXYL)$_{16}$ [8] methanol: ammonium hydroxide (30%) (99:1); (d) DAB-dendrimer-(NH-3-CO-PROXYL)$_{32}$ [9] methanol: ammonium hydroxide (30%) (99:1).

Example 2

In Vivo Pharmacokinetics of Joint Injected With Nitroxyl-Containing Dendrimer Using Magnetic Resonance Imaging (MRI)

Inject into both knee joints of a geriatric male (ca. 65–75 years; 70–80 kg), who has been diagnosed as osteoarthritic and is about to be treated medically for chronic severe pain and inflammation in both knees, 0.5 mL of a stock 100 $\mu$M sterile solution sterile solution in 0.9% normal saline of a dendrimer of Formula (I) containing 32 terminal PROXYL-3-carbamido nitroxide groups [9] using a (gauge 25) needle. Then position the patent in a MR imager (1.5 Tesla MR system, SIGNA; General Electric Medical Systems, Milwaukee, Wis.) and obtain a scan of both knee joints in the conventional manner. At periodic intervals of about a month, repeat the procedure. Compare the succession of MR images thus obtained to evaluate the response of the knee joints to the treatment protocol.

Follow the above procedure in a peri-menopausal female whose blood chemistry indicates she is a high risk candidate for arthritis, taking the first MRI scan of both hip joints as a control before bone density evaluation has shown any significant reduction in bone density. Repeat the process at periodic intervals and initiate hormone replacement therapy when the MRI scans indicate that accelerated reduction in bone density has begun.

Follow the above procedure with a young adult (ca. 20–30 years) diagnosed with a severe case of juvenile rheumatoid arthritis by injection into the joints of the patient most severely affected by the disease to evaluate the response of the patient to a series of aggressive medical treatment protocols.

Follow each of the above procedures but use instead a dendrimer of Formula (I) containing 16 terminal PROXYL-3-carbamido nitroxide groups [8]. The following illustrates the in vivo pharmacokinetics of a joint injected with a nitroxyl-containing dendrimer using MRI in a different end use method.

Into both shoulder joints of a female (ca. 16 years; 45–55 kg), with post-trauma chronic soreness in one of the shoulder joint is injected 1 mL of a stock 100 μM sterile solution in 0.9% normal saline of a dendrimer of Formula (I) containing 32 terminal PROXYL-3-carbamido nitroxide groups [9] using a (gauge 25) needle. Then position the patent in a MR imager (1.5 Tesla MR system, SIGNA; General Electric Medical Systems, Milwaukee, Wis.) and obtain a scan of both joints in the conventional manner. The status of the articular cartilage of the injured shoulder joint compared to the non-injured joint is readily identifiable in the MR image thus obtained of each and provides a standard for comparison for the injury that can be used to follow the progression of the cure.

Example 3

In Vitro Stability of Dendrimer-Containing Nitroxides (Rate of Nitroxide Reduction).

In vitro rate of nitroxide reduction (Table 1) was undertaken using superoxide in the presence of a thiol, as an in vitro model for activated phagocytic cells. G. M. Rosen, B. E. Britigan, M. S. Cohen, S. P. Ellington and M. J. Barber, *Biochim. Biophys. Acta,* 969:236–241, 1988; G. M. Rosen and E. J. Rauckman. *Biochem. Pharmacol.* 26: 675–678, 1977; S. Pou, P. L. Davis, G. L. Wolf and G. M. Rosen, *Free Rad. Res.* 23: 353–364, 1995; and E. Finkelstein, G. M. Rosen and E. J. Rauckman, *Biochim. Biophys. Acta,* 802:90–98, 1984. For these determinations, nitroxides [S. Pou, et al, E. Finkelstein, et al., supra, and H. Kuthan, V. Ullrich and R. Estabrook, *Biochem. J.* 203: 551–558, 1982, (50 micromolar) were added to cysteine (200 micromolar) in the presence of a continued flux of superoxide (10 micromolar/min), generated by the action of xanthine oxidase on xanthine (400 micromolar) in Chelexed sodium phosphate buffer (50 mM, pH 7.4) The rate of superoxide production was estimated by following the superoxide dismutase (30 U/mL) inhibitable reduction of ferricytochrome c at 500 nm using a molar absorbance of 21 mM$^{-1}$ cm$^{-1}$. H. Kuthan et al. supra. Rates of nitroxide reduction were monitored by EPR spectroscopy at ambient temperature by observing the change of the low-field (the broadened EPR spectrum of each dendrimer-linked nitroxide prevented the use of other peaks to measure rates of reduction) as a function of time.

Example 5

In Vivo Pharmacokinetics of Joint Injected With Nitroxyl-Containing Dendrimer Using Magnetic Resonance Imaging (MRI)

Rabbits (2.8–3.5 kg) to be used for MRI experiments are sedated with intramuscular Ketamine and Xylazine. Anesthesia is maintained with i. v. sodium pentobarbital as required. Under fluoroscopic guidance, a needle (gauge 25) is placed into the knee joint of a thus-anesthetized rabbit and 1 mL of a stock solution of a nitroxyl functionalized dendrimer of Formula (I) containing 32 nitroxyl functionalizing groups [9]. The rabbit's injected joint is then positioned in a MR imager. Plastic tubes containing the same dose of the same stock solution of the dendrimer [9] is placed next to the rabbit as standards to demonstrate that changes in the observed MRI intensity is not the result of instrumentation fluctuations but instead arise due to pharmacokinetic changes in the diffusion of the nitroxide [9] from the joint. The articular cartilage of the rabbit are readily identifiable in the MR image thus obtained and provide a standard for comparison with a corresponding joint of another experimental rabbit whose joints have degenerated as a result of artificially-induced inflammation.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a method of enhancing the image obtained by MRI of the joint of an animal which comprises the step of injecting into the joint, prior to or during the MRI scan thereof, in admixture with a non-toxic pharmacologically acceptable sterile aqueous vehicle, a non-toxic amount effective to enhance the MR image thereby obtained by the scan, of a water soluble nitroxyl-functionalized dendrimer which is non-toxic in the amount administered, the improvement wherein (a) the joint exhibits the symptoms of a degenerative joint disease or trauma; (b) the nitroxide is a bio-reductive resistant, positively charged at physiological pH, nitroxyl poly-functionalized dendrimer of Formula (I):

wherein each R independently is either (A) a nitroxyl group of Formula (II):

wherein X is an oxygen atom or two hydrogen atoms, n is the integer 0 or 2, R' is lower alkyl and R" is H or lower alkyl, or (B)

a group of Formula (IV):

wherein each alkylene in Formulae (I), and (IV) is a bridging divalent alkylene group of 2–6 carbon atoms with 2–3 carbon atoms in the chain and R is as defined herein; (c) wherein, for a given R of Formula I, the number of iterations of Formula IV is 0–4, (d) the number of terminal R groups in the dendrimer molecule which are nitroxyl groups of Formula (II) is from 12 to 48; and (e) the dose of the composition which is injected into the joint of such an animal is effective to selectively visualize the proteoglycans of the cartilage present in the joint in the MR image produced by the scan.

2. The method of claim 1, wherein the animal is a human being exhibiting one or more symptoms of osteoarthritis or rheumatoid arthritis.

3. The method of claim 1, wherein the concentration of the dendrimer in the solution is from about 50 to 150 micromolar and the aqueous vehicle is distilled water, physiological saline solution, fluid withdrawn from the joint to be scanned, or a mixture of either of the former two and the latter.

4. The method of claim 1, wherein each of the R groups of Formula (I) is an identical group of Formula (IV) whose R groups are identical to those of Formula (I), and wherein this structural sequence of each R group being an identical group of Formula (IV) whose R groups are identical to those of Formula (I) is repeated until the dendrimer has from 12 to 48 terminal R groups, all of which are identical groups of Formula (II).

5. The method of claim 1, wherein in Formula (II) R' is methyl, R" is H and X is a divalent oxygen atom.

6. The method of claim 1, wherein in Formulae (I), (III) and (IV) alkylene is trimethylene and in Formula (II) R' is methyl, R" is H, n=2 and X is a divalent oxygen atom.

7. The method of claim 6, wherein each of the R groups of Formula (I) is an identical group of Formula (IV) whose R groups are identical to those of Formula (IV), and this structural sequence of each R group being an identical group of Formula (IV) whose R groups also are identical to those of Formula (IV) is repeated until the dendrimer molecule has from 12 to 48 terminal R groups, all of which are identical groups of Formula (II).

8. The method of claim 7, wherein the total number of terminal R groups in the dendrimer molecule is 16 or 32.

9. The method of claim 1, wherein the dendrimer is DAB-dendrimer-(NH-3-CO-PROXYL)$_{32}$.

10. The method of claim 1, wherein the injection and MRI scanning steps are repeated at spaced time intervals for the purpose of evaluating the efficacy of the medical treatment of the trauma or disease.

11. The method of claim 1, wherein the structure of the three R groups in Formula I are: (Formula II)$_2$, (Formula IV, each is Formula II).

12. The method of claim 1, wherein the structure of the three R groups in Formula I are: (Formula II)$_3$.

13. The method of claim 1, wherein the structure of the three R groups in Formula I are: (Formula IV in which each R is Formula II)$_2$, (Formula IV in which each R is Formula IV in which each R is Formula II).

14. The method of claim 1, wherein the structure of the three R groups in Formula I are: (Formula IV in which each R is Formula IV in which each R is Formula II)$_2$, (Formula IV, in which each R is Formula IV, in which each R is Formula IV, in which each R is Formula II).

15. The method of claim 1, wherein the structure of the three R groups in Formula I are: (Formula IV in which each R is Formula IV in which each R is Formula IV in which each R is Formula II)$_2$, (Formula IV, in which each R is Formual IV, in which each R is Formula IV, in which each R is Formula IV, in which each R is Formula II).

\* \* \* \* \*

UNITED STATES PATENT AND TRADEMARK OFFICE
CERTIFICATE OF CORRECTION

PATENT NO. : 6,991,778 B2
APPLICATION NO. : 10/148962
DATED : January 31, 2006
INVENTOR(S) : Gerald M. Rosen It is certified that error appears in the above-identified patent and that said Letters Patent is hereby corrected as shown below:

Column 12, line 41, delete entire formula (III)

"—N-alkylene-R        (III)
   |
   R'''                    "

Column 14, line 26, reads "Formual IV" should read -- Formula IV --

Signed and Sealed this

Tenth Day of July, 2007

JON W. DUDAS
*Director of the United States Patent and Trademark Office*